(12) United States Patent
Liu (10) Patent No.: US 11,324,467 B2
(45) Date of Patent: May 10, 2022

(54) OVERALL FULL-ANGLE COINCIDENCE BRAIN PET DETECTOR AND OVERALL APPARATUS

(71) Applicant: SHANDONG MADIC TECHNOLOGY CO., LTD., Linyi (CN)

(72) Inventor: Jiguo Liu, Linyi (CN)

(73) Assignee: SHANDONG MADIC TECHNOLOGY CO., LTD., Linyi (CN)

( * ) Notice: Subject to any disclaimer, the term of this patent is extended or adjusted under 35 U.S.C. 154(b) by 0 days.

(21) Appl. No.: 17/053,968

(22) PCT Filed: Apr. 1, 2019

(86) PCT No.: PCT/CN2019/080784
§ 371 (c)(1),
(2) Date: Nov. 9, 2020

(87) PCT Pub. No.: WO2020/015384
PCT Pub. Date: Jan. 23, 2020

(65) Prior Publication Data
US 2021/0267565 A1 Sep. 2, 2021

(30) Foreign Application Priority Data
Jul. 17, 2018 (CN) .......................... 201810785726.9

(51) Int. Cl.
*G01N 23/00* (2006.01)
*A61B 6/00* (2006.01)
(Continued)

(52) U.S. Cl.
CPC .............. *A61B 6/501* (2013.01); *A61B 6/037* (2013.01); *G01T 1/2023* (2013.01); *A61B 2562/046* (2013.01)

(58) Field of Classification Search
CPC ... A61B 6/501; A61B 6/037; A61B 2562/046; G01T 1/2023
See application file for complete search history.

(56) References Cited

U.S. PATENT DOCUMENTS 6,225,631 B1   5/2001  Mastrippolito et al.
9,606,245 B1 * 3/2017  Czarnecki ............. G01T 1/1642
(Continued)

FOREIGN PATENT DOCUMENTS

CN   103536308 A   1/2014
CN   103543463 A   1/2014
(Continued)

OTHER PUBLICATIONS

Ahmed et al., "Sensitivity comparison of the helmet-chin PET with a cylindrical PET; asimulation study", IEEE Nuclear Science Symposium and Medical Imaging Conference, 3 pages. (Year: 2015).*
(Continued)

*Primary Examiner* — Kiho Kim
(74) *Attorney, Agent, or Firm* — Scully, Scott, Murphy & Presser, P.C.

(57) ABSTRACT

A full-angle coincidence brain PET detector and apparatus, including a plurality of PET detection modules, each of which includes PET detection crystals, a photoelectric sensor array and light guides, all the detection crystals being arranged towards a cavity. The detection modules form a chamber having an opening, each dimension of the cavity is no greater than 35-50 cm, the opening is located at a lower side of the chamber. A cross-sectional area at the opening is greater than a maximum cross-sectional area of a head in a horizontal direction. Except for the opening, all the detection modules are non-detachably connected together. All cross-sectional areas of gaps between the detection modules are less than ½ to ⅓ of the area of the smallest one of the detection crystals. At least 75% to 80% of a coincidence (Continued)

event occurring at a center of the chamber is detected by the detection modules.

6 Claims, 5 Drawing Sheets

(51) Int. Cl.
*A61B 6/03* (2006.01)
*G01T 1/202* (2006.01)

(56) References Cited

U.S. PATENT DOCUMENTS

| | | | |
|---|---|---|---|
| 2008/0042067 | A1 | 2/2008 | Rousso et al. |
| 2015/0115162 | A1 | 4/2015 | Tashima et al. |
| 2016/0166219 | A1 | 6/2016 | Majewski et al. |
| 2017/0119325 | A1* | 5/2017 | Tamura ............... A61B 6/4241 |
| 2017/0215822 | A1 | 8/2017 | Da Rocha Vaz Pato et al. |
| 2018/0338697 | A1* | 11/2018 | Sackellares .......... A61B 5/6803 |
| 2020/0305811 | A1* | 10/2020 | Benlloch Baviera ....................... A61B 6/4275 |

FOREIGN PATENT DOCUMENTS

| | | |
|---|---|---|
| CN | 105559811 A | 5/2016 |
| CN | 106950587 A | 7/2017 |
| CN | 107550512 A | 1/2018 |
| CN | 107595316 A | 1/2018 |
| JP | 2007-218768 A | 8/2007 |
| JP | 2009-031304 A | 2/2009 |
| JP | 2010-197140 A | 9/2010 |
| JP | 2015-007636 A | 1/2015 |
| JP | 2015-087260 A | 5/2015 |
| JP | 6385131 B2 | 9/2018 |
| WO | 2009/125480 A1 | 10/2009 |
| WO | 2011/111119 A1 | 9/2011 |
| WO | 2017/186993 A1 | 11/2017 |

OTHER PUBLICATIONS

Tashima et al., "Development of the helmet-chin PET prototype," IEEE Nuclear Science Symposium and Medical Imaging Conference, 3 pages. (Year: 2015).*

International Search Report dated Jun. 27, 2019 received in International Application No. PCT/CN2019/080784.

First Office Action dated Dec. 25, 2019 received in Chinese Patent Application No. 201810785726.9 together with an English language translation.

* cited by examiner

FIG. 10

OVERALL FULL-ANGLE COINCIDENCE BRAIN PET DETECTOR AND OVERALL APPARATUS

TECHNICAL FIELD

The present disclosure relates to the technical field of PET detectors, and in particular to a dedicated PET detector with extremely strong wrapping ability and an overall apparatus thereof, an overall full-angle coincidence brain PET detector and an overall apparatus thereof, none of which was ever seen in the related art.

BACKGROUND

Positron Emission Tomography (PET) apparatuses are widely used in specificity imaging of animals and human bodies (hereinafter referred to as scanned object). In PET imaging, it is required to first inject a tracer labeled with a positron nuclide into the scanned object, and then image the distribution of the tracer in the scanned object. The imaging of the position labeled by the tracer has strong specificity, and dynamic imaging may be performed with a high degree of recognition, which is currently one of the imaging means with the highest degree of recognition.

A general idea of PET apparatus is to design it as a detector ring with the length/depth increased at most. Traditional PET apparatuses have insufficient axial depth of the detector and can only scan a limited local area. There are two problems with this imaging method: first, the imaging speed is slow, each bed takes 1 to 5 minutes, the axial field of view is about 20 cm, and additional calculation time is further required; second, one of the major advantages of PET is that dynamic information of the tracer can be obtained, but it is impossible for the detector with insufficient depth to obtain the dynamic information of the tracer on the whole body. Taking the brain as an example, if the dynamic information of the neck or forehead is desired, it is impossible to obtain it. Existing head detector rings can only obtain the dynamic information of a middle position of the head.

Figure 2:
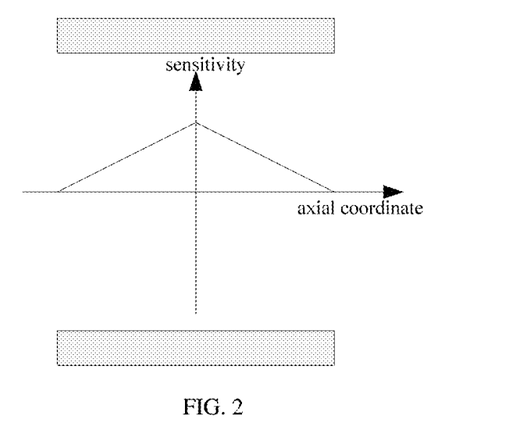
FIG. 2 is a schematic diagram showing that the axially extended detector ring has different sensitivities to various internal parts.
Figure 3:
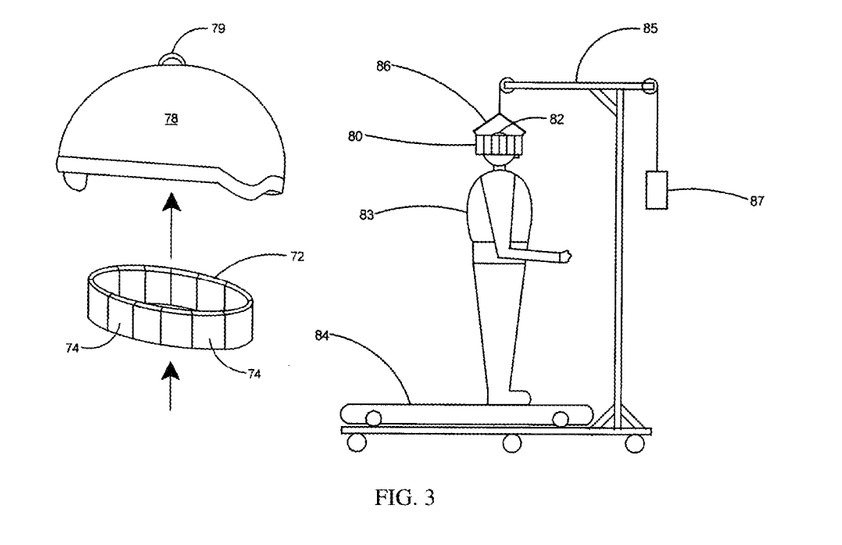
FIG. 3 is a schematic diagram of a helmet-shaped brain PET.
Figure 4:
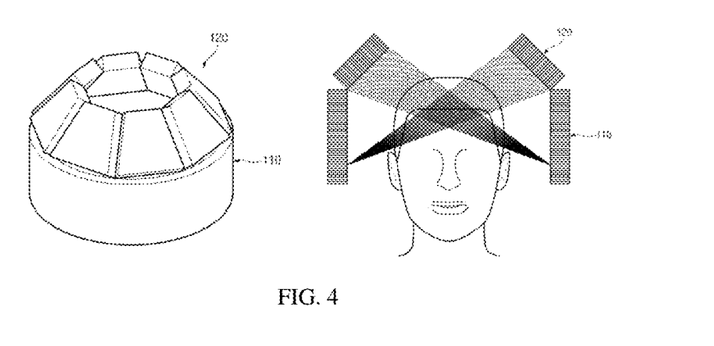
FIG. 4 is a schematic diagram of a brain PET scheme having a top tilted detector added.
Figure 5:
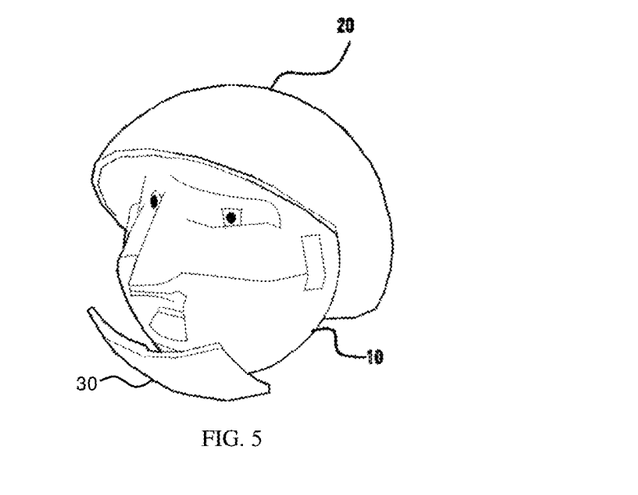
FIG. 5 is a schematic diagram of a helmet with a chin detector piece.

The problem with such detector ring design is that the sensitivity in the scanning field of view is not uniform enough. The sensitivity is the highest in the middle of the overall detector. As the position moves from a center to both ends of the detector along an axis, the sensitivity drops rapidly, and drops to a very low level at the positions of the two ends of the detector, or even zero. FIG. 2 shows an extended PET apparatus in the related art.

The reason for this phenomenon is that PET adopts a data acquisition method of coincidence detection. When 511 keV gamma rays are simultaneously detected on two exactly opposite detector crystals, this is called a true coincidence event. Only in this situation will the two gamma rays be taken as an effective positron event. Occurrence positions of this positron event are on a straight line between the two crystals, which are positions to be detected. This line is called line of reaction, hereinafter referred to as LOR.

Figure 1:
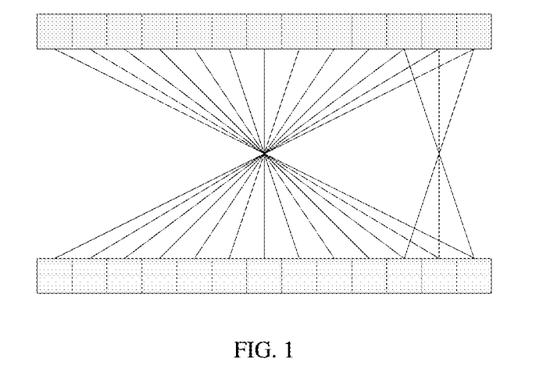
FIG. 1 is a schematic diagram showing that LORs of different detection points in an axially lengthened detector ring can be captured.

FIG. 1 is a schematic diagram of the LORs of a PET detector in the related art. It can be clearly seen from a comparison between two occurrence positions in the figure that one position is at the center of the axial field of view of the detector, and the other position is not at the center of the axial field of view, but at the edge. Due to the difference in position, the probabilities of detecting LORs occurring from different positions differ greatly. For most LORs that occur from the center, they can be detected as long as they are not horizontal or nearly horizontal; for LORs occurring from the edge, only some LORs that are perpendicular or nearly perpendicular to the axial direction can be detected. The number of LORs that can be detected occurring from non-center positions is significantly lower than the number of LORs occurring from the center, which leads to the fact that the sensitivity becomes lower and lower as the occurrence position deviates from the LOR center. The sensitivity of any point in the PET field of view is determined by a solid angle covered by all LORs passing through the point. The larger the solid angle covered by the LORs is, the greater the sensitivity of the point will be. This relationship between the sensitivity and the position is shown in FIG. 2, which shows that the closer it is to the center of gravity, the higher the sensitivity will be; on the contrary, the sensitivity at the edge is very low.

A clinical whole-body PET apparatus has a large aperture. On one hand, its sensitivity is too low, so the scanning time for a single bed is usually several minutes. On the other hand, due to the non-collinearity of the gamma ray pair itself generated by positron annihilation, the spatial resolution is limited, making it unsuitable for dedicated brain detection. The reason for this phenomenon is that PET adopts a data acquisition method of coincidence detection. When 511 keV gamma rays are simultaneously detected on two exactly opposite detector crystals, this is called a true coincidence event. Only in this situation will the two gamma rays be taken as an effective positron event. Occurrence positions of this positron event are on a straight line between the two crystals, which are positions to be detected. This line is called line of reaction, hereinafter referred to as LOR. FIG. 1 is a schematic diagram of the LORs of a PET detector in the related art. It can be clearly seen from a comparison between two occurrence positions in the figure that one position is at the center of the axial field of view of the detector, and the other position is not at the center of the axial field of view, but at the edge. Due to the difference in position, the probabilities of detecting LORs occurring from different positions differ greatly. For most LORs that occur from the center, they can be detected as long as they are not horizontal or nearly horizontal; for LORs occurring from the edge, only some LORs that are perpendicular or nearly perpendicular to the axial direction can be detected. The number of LORs that can be detected occurring from non-center positions is significantly lower than the number of LORs occurring from the center, which leads to the fact that the sensitivity becomes lower and lower as the occurrence position deviates from the LOR center. The sensitivity of any point in the PET field of view is determined by a solid angle covered by all LORs passing through the point. The larger the solid angle covered by the LORs is, the greater the sensitivity of the point will be. This relationship between the sensitivity and the position is shown in FIG. 2, which shows that the closer it is to the center of gravity, the higher the sensitivity will be; on the contrary, the sensitivity at the edge is very low. At the same time, since the detector ring generally used to detect the body is too large, if it is used to detect the brain, the effective sensitivity angle is actually very small, which may only be between 5°-10°, and which also results in very little image information obtained corresponding to the LOR, making it substantially impossible to form effective recognizable PET image information.

Therefore, a dedicated brain PET apparatus is produced. The aperture of the dedicated brain PET apparatus is much smaller than that of a whole-body PET, which effectively reduces the influence of non-collinearity on the resolution. At the same time, people have tried to propose various solutions to improve the sensitivity of PET apparatus. There are two ways to increase the sensitivity, i.e., increasing the thickness of the detector and increasing the solid angle of the detector. Since the increase of the thickness of the detector will reduce the accuracy of gamma ray positioning (parallel error) to thereby reduce the spatial resolution, increasing the solid angle of the detector becomes a more important solution.

Existing brain PET designs mainly include the following ones: Helmet-shaped brain PET: U.S. Pat. No. 7,884,331B2. In a detector of this design, a circular design similar to the whole-body PET is adopted, and a detector ring is installed on the helmet. The nature of the design of this detector is the same as that of human body PET detectors. They are both circular detectors. The main innovation lies in the installation method of the detector ring. Because the detector ring is designed to be smaller and closer to the head, it can achieve certain improvement on the effect. However, since the upper helmet part is only used for wearing and has no detector function, there is actually no substantive technical advancement. From the perspective of effective sensitivity, for 360°, about 30°-40° be covered at most, and $11/12$ of the LORs still cannot be detected.

Addition of inwardly tilted detector: U.S. Pat. No. 9,529,100B2. In this document, an inwardly tilted top detector array is added above the traditional detector ring to cover a larger solid angle. However, there are two problems with this design. First, the top detectors do not cover the top of the head; second, the lower detector ring does not cover the part below the jaw, so its solid angle is still limited. From the perspective of effective sensitivity, for 360°, about 80°-120° be covered at most, and more than $2/3$ of the LORs still cannot be detected.

Addition of chin detector: U.S. Pat. No. 9,226,717B2. In this invention, the detectors are divided into two parts: a helmet-shaped detector and a chin detector. By adding the chin detector, a larger solid angle can be covered. In this invention, in order to eliminate the claustrophobic feeling of the patient, a lower edge of the front portion of the helmet-shaped detector is above the eyes of the patient, so there is no detector directly in front of the patient's face, and its sensitivity is therefore still limited. The angle covered by the helmet is less than a half, and the chin detector is only a small piece. The enhancement of the complement of the overall LORs is very limited. From the perspective of effective sensitivity, for 360°, about 160°-180° be covered at most, and more than $1/2$ of the LORs still cannot be detected. In this document, the chin detector piece is also expanded, but the expanded detector still has the eyes exposed on the upper helmet part. In addition, with the larger chin piece, the actual effective detection angle is only about 200°, and a lot of LORs still cannot be captured.

In summary, the brain PETs in the related art have insufficient coverage of the entire head, uneven sensitivity, and insufficient ability to capture the exposed parts of the LORs. A difference in the effect of generating dynamic images is particularly obvious. For the above related art, for example, if it is desired to obtain PET dynamic images of an oral cavity or brain stem, clear images cannot be obtained using the above technologies, and the results cannot be used for observation; that is, PET images of many areas of the head, especially many areas in the lower half of the head cannot be well obtained. This problem cannot be solved by only relying on the existing detector rings or helmet type detectors. They cannot fundamentally solve the problem of one-time clear PET imaging of the head or one-time PET dynamic imaging of the entire head.

SUMMARY

An object of the present disclosure is to solve the problems in the related art that the PET detectors for the head/brain have insufficient wrapping ability and insufficient overall sensitivity, and to provide a simplified and perfect solution for this situation where there is no effective solution yet. With this arrangement, credible whole brain PET images can be obtained at one time through an apparatus with the smallest size possible. This solution to the problem has not yet appeared in the relate art, and even the problem of sensitivity defect has not yet been clearly raised in the related art. As compared with adding a detector piece or constantly increasing the size of the detector ring, the solution of the present application has higher pertinency and more cost-effective. As compared with the existing brain PET apparatuses in the related art, it has significantly stronger wrapping ability and higher sensitivity, and the effect is very good. In the related art, there is generally no detector arranged beyond the upper half of the head, which is extremely disadvantageous for detecting the lower half of the head in a single detection; even if it is only for the brain, since the opening of detection cavity is too large, a capture rate of LORs is also low even for the upper part of head, which cannot achieve good detection results.

The present disclosure provides an overall full-angle coincidence brain PET detector, which includes a plurality of PET detection modules, and each of the PET detection modules is composed of PET detection crystals, a photoelectric sensor array and a light guide. The PET detection crystals are each arranged in a direction toward an interior of a detection cavity; the plurality of PET detection modules are adjacent to each other to form the detection cavity with an opening, and the length, width and height of an inner cavity of the detection cavity are no larger than 35-50 cm each. The opening of the detection cavity is located below the detection cavity; the cross-sectional area at the opening is larger than the maximum cross-sectional area of human head in the horizontal direction; except for the opening, all the plurality of PET detection modules are non-detachably connected together; the cross-sectional area of each of gaps between the plurality of PET detection modules is less than $1/2$-$1/3$ of the area of the smallest one of the PET detection crystals.

A detection coverage of the detection cavity for true coincidence events reaches such a degree that at least 75%-80% of the true coincidence events occurring from the center of the detection cavity are detected by the plurality of PET detection modules.

The detection cavity is of a sphere shape or an ellipsoid shape; the sphere shape specifically means that axes of all the PET detection modules pass through a center of the sphere, and distances from centers of inner surfaces of all the PET detection modules to the center of the sphere are equal or have an error within 8 mm; and the ellipsoid shape specifically means that an ellipsoid shape with c>a=b is formed in the inner cavity of the detection cavity.

The detection cavity is formed by splicing two portions with different geometric shapes, i.e., a top and a body; the body has one of the following shapes: a shape of a middle part of a sphere, or a shape of an ellipsoid with c>a=b and a part of the top and a part of the bottom removed respectively, or a shape of a regular polygonal prism, or a shape of a cylinder, or a shape of a downwardly tapering truncated cone, or a shape of an upwardly tapering truncated cone, or a shape of a downwardly tapering regular polygonal pyramid, or a shape of an upwardly tapering regular polygonal pyramid; the top is a planar end cap, or an inner cavity of the top is a part of a spherical surface, or an inner cavity of the top is a part of an ellipsoidal surface with a:b:c at any ratio, and the largest continuous gap formed between the top and the body is also less than ½-⅓ of the area of the smallest one of the PET detection crystals.

A coincidence circuit is connected between every two PET detection modules; each of the PET detection modules has the following specific structure: a detector housing, a photoelectric sensor array, a light guide, and PET detection crystals are sequentially arranged from outside to inside. The light guide is tightly coupled with both the photoelectric sensor array and the PET detection crystal; the material of the PET detection crystals is a scintillation crystal, which is composed of one or more crystal blocks; the regular polygonal prism is a regular hexagonal prism or a regular octagonal prism, and the regular polygonal pyramid is a regular quadrangular pyramid or a regular hexagonal pyramid; a circular ring-shaped shielding plate is attached closely against a lower edge of the body, and the material of the shielding plate is stainless steel or boron-containing plastic or lead-containing plastic. The shielding plate is formed by splicing two to five sub-plates having exactly the same shape.

Several PET detection modules that are slightly higher on the front portion of the detection cavity are removed to form an opening suitable for both eyes to observe outward.

Inward faces of the PET detection crystals are planar or nearly planar, and the shapes are square or rectangle; the crystal block is specifically a crystal strip array composed of a plurality of crystal strips, or is composed of one or more integrally cut crystals. The material of the scintillation crystal is selected from one or more of bismuth germanate (BGO) crystals, sodium iodide (NaI) crystals, NaI(Tl) single crystals, lutetium silicate (LSO) crystals, gadolinium silicate (GSO) crystals and yttrium lutetium silicate (LYSO); spacers made of high atomic number substance are installed between all the detection module rings, or spacers made of high atomic number substance are installed between some of the detection module rings, or no spacers are installed between all the detection module rings; the high atomic number substance is lead or tungsten; the regular polygonal prism is a regular hexagonal prism or a regular octagonal prism, and the regular polygon is a regular hexagon or a regular octagon.

The crystal strip array is composed of a plurality of crystal strips; each of the one or more crystal blocks is composed of one or more integrally cut crystals.

For the convenience and necessity of overall implementation, the present disclosure also provides a full-angle coincidence PET detection apparatus, which includes the full-angle coincidence PET detector as described above, and which further includes a support member, a power supply circuit, a communication line, and a PC terminal; wherein the support member fixes and supports all the plurality of PET detection modules on the aforementioned detection cavity, and the support member can drive the detection cavity to rotate at any angle, or drive the detection cavity to translate toward any direction; the PC terminal is equipped with a PET signal acquisition and operation analysis system; the power supply circuit provides an electrical energy under a rated voltage to the support member and all the PET detection modules; and the communication line transmits signals detected by all the PET detection modules to the aforementioned PET signal acquisition and operation analysis system.

The present disclosure has the following three main advantages: first, for the PET apparatus for general inspection of the whole body, the actual crystals used are relatively fewer, but a very good detection effect is achieved; not only a one-time clear imaging can be performed on the head, but also a dynamic image of the entire head can even be formed at one time. Second, for some existing PET detectors for the brain, their design ideas are still affected by the old methods; not only the design method does not have high pertinency, but also the problem of insufficient capture of the overall sensitivity of the head is not paid attention to, especially for the lower part of the head; however, for the oral cavity, nasopharynx, and brain stem in the lower part, image capture thereof is very important, so the present disclosure is of great significance. Third, in terms of the application, the present disclosure is manufactured in the simplest and intensive way, in which only one cavity is formed. For example, by covering the head from top to bottom, the PET scanning of the head can be completed. This method is not only simple and effective, but also has a smaller amount of expensive crystals used, which is very economical and achieves a very good effect. None of the above was ever seen or accomplished in the related art.

BRIEF DESCRIPTION OF THE DRAWINGS

The accompanying drawings required to be used in the description of the embodiments of the present disclosure or the related art are described briefly below, so that the technical solutions according to the embodiments of the present disclosure or according to the related art will become clearer. It is apparent that the accompanying drawings in the following description show only some embodiments of the present disclosure. For those skilled in the art, other accompanying drawings may also be obtained according to these drawings provided, without any creative work.

The devices corresponding to the reference signs are: 1: detector; 2: head; 3: detection cavity; 4: opening; 5: top; 6: body; 7: PET detection module; 8: photoelectric sensor array; 9: light guide; 10: PET detection crystal.

DETAILED DESCRIPTION

Preferred embodiments of the present disclosure will be described in detail below with reference to the accompanying drawings, so that the advantages and features of the present disclosure can be more easily understood by those skilled in the art, thereby making a clearer and definite definition of the scope of protection of the present disclosure.

First Embodiment

An overall full-angle coincidence brain PET detector includes a plurality of PET detection modules, and each of the PET detection modules is composed of PET detection crystals, a photoelectric sensor array and a light guide. The PET detection crystals are each arranged in a direction toward an interior of a detection cavity; the plurality of PET detection modules are adjacent to each other to form the detection cavity with an opening, and the length, width and height of an inner cavity of the detection cavity are no larger than 35-50 cm each. The opening of the detection cavity is located below the detection cavity; the cross-sectional area of the opening is larger than the maximum cross-sectional area of human head in the horizontal direction; except for the opening, all the plurality of PET detection modules are non-detachably connected together; the cross-sectional area of each of gaps between the plurality of PET detection modules is less than ½-⅓ of the area of the smallest one of the PET detection crystals. Herein, the length, width and height are no larger than 35-50 cm each, and the specific upper limit may be 35/38/41/44/47/50 cm.

The detector may be made into a suitable detection mask that does not affect radiation, such as being made of engineering plastic, transparent or translucent resin, and is suitable for the installation of the above plurality of PET detection modules. All the detection modules are inserted inward into corresponding preset positions on the detection mask so that the detector is formed, and the on-site assembly is simple and convenient.

A detection coverage of the detection cavity for true coincidence events reaches such a degree that at least 75%-80% of the true coincidence events occurring from the center of the detection cavity are detected by the plurality of PET detection modules. For example, the ratio is 76%, 77% or 78%. This design ensures the capture rate of true coincidence events. As compared with the related art, only the upper part of the head is wrapped tightly. However, according to the PET capture principle, the capture rate of LORs is about 50% at most.

The detection cavity is of a sphere shape or an ellipsoid shape; the sphere shape specifically means that axes of all the PET detection modules pass through a center of the sphere, and distances from centers of inner surfaces of all the PET detection modules to the center of the sphere are equal or have an error within 8 mm From the point of view of the design principle, it is best for the axes of all the modules to pass through the center of the sphere, but there will inevitably be errors in reality. If the error is within 8 mm, it is also acceptable. In addition, if the axis of the surface of the detection module does not pass through the center of the detector and has a deviation from the center which is within 1 cm, it is acceptable. The ellipsoid shape specifically means that an ellipsoid shape with c>a=b is formed in the inner cavity of the detection cavity. Herein, for the application of head detection, the ellipsoid shape with c>a=b is more suitable, and the ellipsoid shape with a>c=b and the ellipsoid shape with b>a=c are also applicable; however, due to the general size of the head, the latter two shapes have little practical significance in application.

The detection cavity is formed by splicing two portions with different geometric shapes, i.e., a top and a body; the body has one of the following shapes: a shape of a middle part of a sphere, or a shape of an ellipsoid with c>a=b and a part of the top and a part of the bottom removed respectively, or a shape of a regular polygonal prism, or a shape of a cylinder, or a shape of a downwardly tapering truncated cone, or a shape of an upwardly tapering truncated cone, or a shape of a downwardly tapering regular polygonal pyramid, or a shape of an upwardly tapering regular polygonal pyramid; the top is a planar end cap, or an inner cavity of the top is a part of a spherical surface, or an inner cavity of the top is a part of an ellipsoidal surface with a:b:c at any ratio, and the largest continuous gap formed between the top and the body is also less than ½-⅓ of the area of the smallest one of the PET detection crystals, e.g., ⅓. The detection cavity must be able to hold an object of the size of the head, but in most cases, if a spherical or ellipsoidal shape is purely used, the upper part is actually relatively empty, which is not advantageous for saving costs. After all, the cost of the detection module is not low, so the body and the relatively flat top which have different shapes are combined to achieve the detection effect while also effectively saving costs.

A coincidence circuit is connected between every two PET detection modules; each of the PET detection modules has the following specific structure: a detector housing, a photoelectric sensor array, a light guide, and PET detection crystals are sequentially arranged from outside to inside. The light guide is tightly coupled with both the photoelectric sensor array and the PET detection crystal; the material of the PET detection crystals is a scintillation crystal, which is composed of one or more crystal blocks; the regular polygonal prism is a regular hexagonal prism or a regular octagonal prism, and the regular polygonal pyramid is a regular quadrangular pyramid or a regular hexagonal pyramid; a circular ring-shaped shielding plate is attached closely against a lower edge of the body, and the material of the shielding plate is stainless steel or boron-containing plastic or lead-containing plastic. The shielding plate is formed by splicing two to five sub-plates having exactly the same shape. The shielding plate here is also the originality of the present disclosure. The radiation of PET also has a significant impact on the human body, and the human body has to be protected from the radiation. Due to the structure of the human body, space must be left for the neck. The above-mentioned flail-like ring-shaped shielding plate can maximally reduce the radiation effect of PET on human body, and it is also convenient to disassemble and assemble. The circular ring-shaped shielding plate may be provided with a buckle suitable for matching with the lower edge of the detection mask so as to facilitate disassembly and assembly. For example, the shielding plate may be two symmetrical pieces, which are installed after the head enters the detection cavity.

Several PET detection modules that are slightly higher on the front portion of the detection cavity are removed to form an opening suitable for both eyes to observe outward. Herein, for the opening suitable for both eyes to observe outward, it is possible to design the sizes and positions of the peripheral detection modules during the design of the detection cavity, that is, they are preset; or it may also be possible to, after the detection modules of the overall detection cavity are arranged and the detection mask is designed, remove some of the detection modules or replace them with detection modules with smaller areas.

Inward faces of the PET detection crystals are planar or nearly planar, and the shapes are square or rectangle; the crystal block is specifically a crystal strip array composed of a plurality of crystal strips, or is composed of one or more integrally cut crystals. The material of the scintillation crystal is selected from one or more of bismuth germanate (BGO) crystals, sodium iodide (NaI) crystals, NaI(Tl) single crystals, lutetium silicate (LSO) crystals, gadolinium silicate (GSO) crystals and yttrium lutetium silicate (LYSO); spacers made of high atomic number substance are installed between all the detection module rings, or spacers made of high atomic number substance are installed between some of the detection module rings, or no spacers are installed between all the detection module rings; the high atomic number substance is lead or tungsten; the regular polygonal prism is a regular hexagonal prism or a regular octagonal prism, and the regular polygon is a regular hexagon or a regular octagon.

The above-mentioned crystals are not exhaustive. The inventive and innovative aspects of the present application are not in the material itself, and all the existing and future crystals can be used in the present application.

The crystal strip array is composed of a plurality of crystal strips; each of the one or more crystal blocks is composed of one or more integrally cut crystals.

For the convenience and necessity of overall implementation, the present disclosure also provides a full-angle coincidence PET detection apparatus, which includes the full-angle coincidence PET detector as described above, and which further includes a support member, a power supply circuit, a communication line, and a PC terminal; wherein the support member fixes and supports all the plurality of PET detection modules on the aforementioned detection cavity, and the support member can drive the detection cavity to rotate at any angle, or drive the detection cavity to translate toward any direction; the PC terminal is equipped with a PET signal acquisition and operation analysis system; the power supply circuit provides an electrical energy under a rated voltage to the support member and all the PET detection modules; the communication line transmits signals detected by all the PET detection modules to the aforementioned PET signal acquisition and operation analysis system. The relatively flexible arrangement of the above-mentioned support member also makes it possible to use it in actual detection.

Second Embodiment

Figure 6:
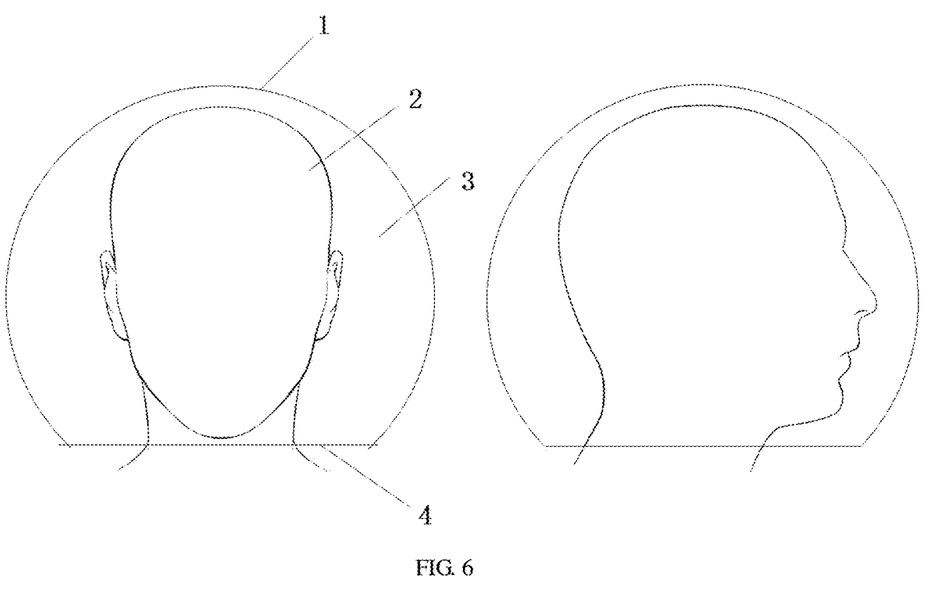
FIG. 6 is a schematic diagram of a detector with a spherical overall structure.

As shown in FIG. 6, the detector of this embodiment is formed into a spherical overall structure, which can be sleeved over the head. Only the horizontally cut opening is exposed on the lower side. Of course, horizontal cutting is not necessarily required, and the modules may not be flush with each other at the opening. This mechanism has the following advantages: the design is simple, the detection modules can have only one size, and the detection mask is also very easy to design; various angles are the same, and only the lower part needs to be opened. The disadvantage is that after the human head enters laterally, since the human heads are mostly longer in the up-and-down direction and the diameter of the lateral cross-section is not so large, the arrangement of the lateral horizontal modules is somewhat wasteful, and such a large space is not required.

Third Embodiment

Figure 7:
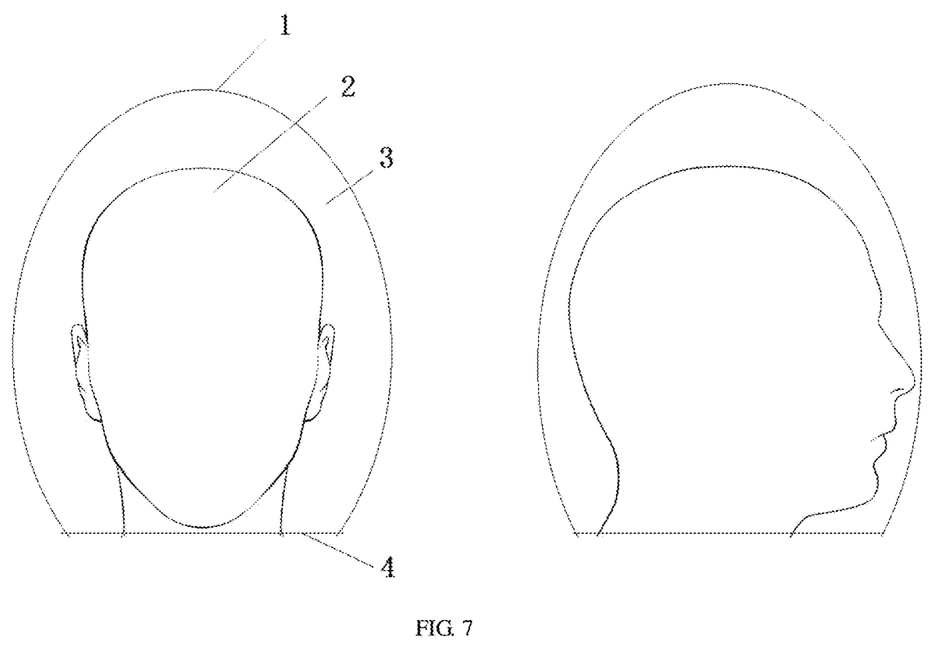
FIG. 7 is a schematic diagram of a detector with an ellipsoidal overall structure.

As shown in FIG. 7, the detector of this embodiment is formed into an ellipsoid shape with C>a=b, which can be sleeved over the head. Only the horizontally cut opening is exposed on the lower side. Of course, horizontal cutting is not necessarily required, and the modules may not be flush with each other at the opening. This mechanism has the following advantages: the design is simple, the detection modules can have only two to three sizes, and the detection mask is also very easy to design; various angles are the same, and only the lower part needs to be opened. The disadvantage is that after the human head enters laterally, for the situation of insufficient longitudinal length, the arrangement of the modules located above is somewhat wasteful, and such a large space is not required.

Fourth Embodiment

Figure 8:
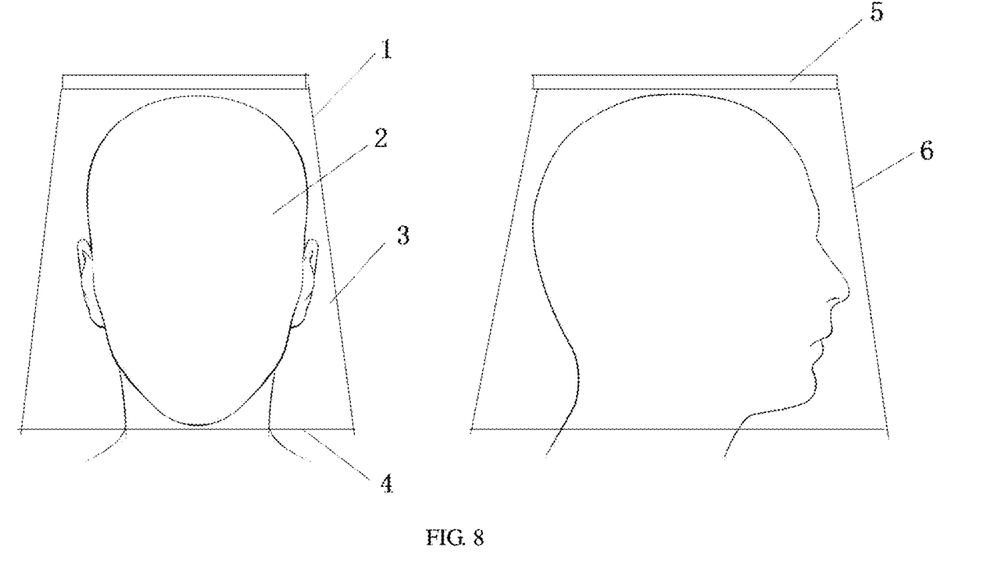
FIG. 8 is a schematic diagram of a detector with a bucket-shaped overall structure.

As shown in FIG. 8, the detector of this embodiment is formed into an inverted bucket shape, which can be sleeved over the head. Only the horizontally cut opening is exposed on the lower side. Of course, horizontal cutting is not necessarily required, and the modules may not be flush with each other at the opening. This mechanism has the following advantages: the design is simple, and the detection modules can have only two to three sizes. For example, the side surface is designed as a trapezoidal surface and a rectangular surface, and the top is designed as a rectangular surface and a triangular or fan-shaped surface to form an approximately circular top. The design of the detection mask is slightly more complicated, and it is necessary to consider the need to install the above five modules of different sizes. The advantage of this structure is that it is easy to access because of the large opening below. The disadvantage is that the large opening below leads to a decrease in the capture rate of LORs, which is close to the lower limit of 75%. At the same time, if the head is too long in the c-axis direction, the capture rate of LORs will be greatly reduced, and this configuration cannot even be used.

Fifth Embodiment

Figure 9:
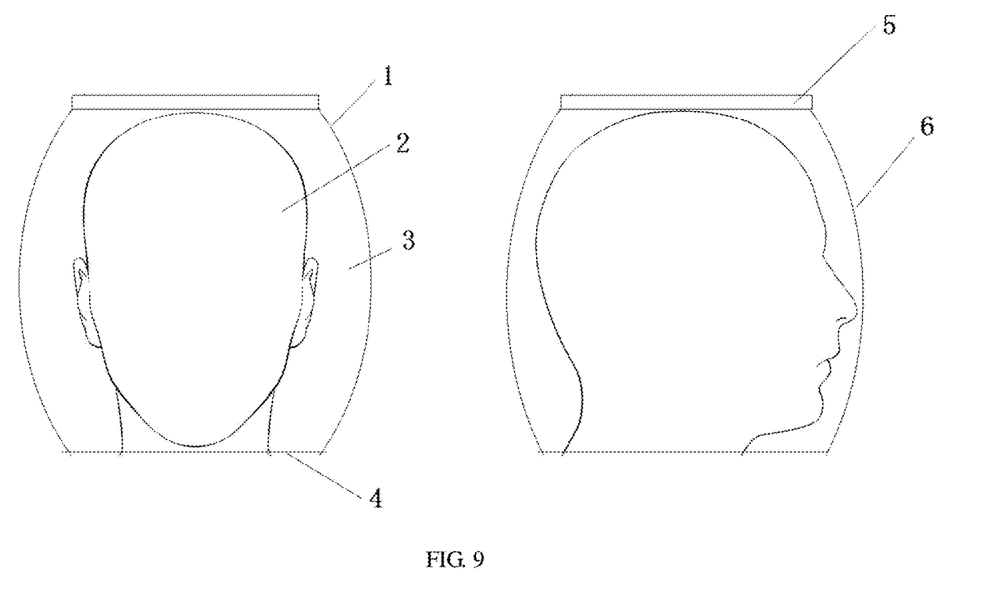
FIG. 9 is a schematic diagram of a detector with a drum-shaped overall structure.
Figure 10:
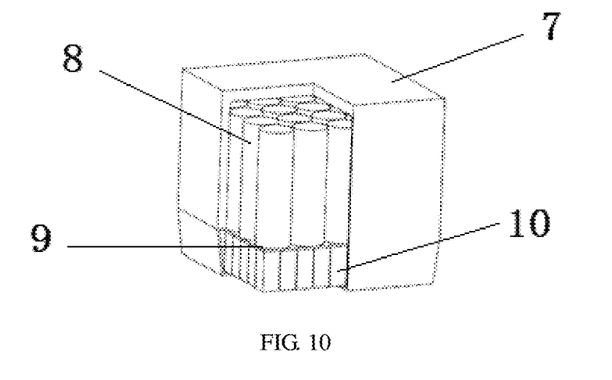
FIG. 10 is a schematic diagram of the structure of a PET detection module.

As shown in FIG. 9, the detector of this embodiment is formed into an ellipsoid shape with C>a=b and having a flat-plate top, which can be sleeved over the head. Only the horizontally cut opening is exposed on the lower side. Of course, horizontal cutting is not necessarily required, and the modules may not be flush with each other at the opening. This mechanism has the following advantages: the design is simple, and the detection modules can have only two to three sizes. For example, the side surface is designed as a trapezoidal surface and a rectangular surface, and the top is designed as a rectangular surface and a triangular or fan-shaped surface to form an approximately circular top. The design of the detection mask is slightly more complicated, and it is necessary to consider the need to install the above five modules of different sizes. The advantage of this structure is crystal-saving since the overall design is more space-saving. The disadvantage is that the opening below is mostly not wide and large enough, which brings difficulty to the entry. At the same time, if the head is too long in the a-axis, b-axis and c-axis directions, it will be difficult for the head to enter, and this configuration cannot even be used.

In terms of shape configuration, various forms of body and top matching may be used for the present application, as described in the first embodiment; the forms are not limited to the description of the second to fifth embodiments, since there are many such forms that cannot be exhaustively listed herein. However, there is no difficulty in implementation herein, and all the implementations will fall within the scope of protection of the present application. The support member is not shown in FIGS. 6-9, but the technology in the field is sufficient to be applied according to the foregoing description without technical obstacles to the implementation.

Described above are only specific embodiments of the present disclosure, but the scope of protection of the present disclosure is not limited to this. Any change or replacement that can be contemplated without creative work should be covered within the scope of protection of the present disclosure. Therefore, the scope of protection of the present disclosure shall be accorded with the scope of the claims.

The invention claimed is:

1. An overall full-angle coincidence brain PET detector, comprising:
a plurality of PET detection modules, each of which comprising:
PET detection crystals,
a photoelectric sensor array, and
a light guide,
wherein the PET detection crystals being each arranged in a direction toward an interior of a detection cavity;
wherein the plurality of PET detection modules are adjacent to each other to form the detection cavity with an opening, a length, width and height of an inner cavity of the detection cavity are no larger than 35-50 cm each, the opening of the detection cavity is located below the detection cavity, and the cross-sectional area at the opening is larger than a maximum cross-sectional area of human head in a horizontal direction;
wherein except for the opening, all the plurality of PET detection modules are non-detachably connected together; and a cross-sectional area of each of gaps between the plurality of PET detection modules is less than ½-⅓ of an area of a smallest one of the PET detection crystals;
a detection coverage of the detection cavity for true coincidence events reaches such a degree that at least 75%-80% of the true coincidence events occurring from a center of the detection cavity are detected by the plurality of PET detection modules;
the detection cavity is formed by splicing a top and a body with different geometric shapes;
the body has one of a shape of a middle part of a sphere, a shape of an ellipsoid with c>a=b and a part of the top and a part of the bottom removed respectively, a shape of a regular polygonal prism, a shape of a cylinder, a shape of a downwardly tapering truncated cone, a shape of an upwardly tapering truncated cone, a shape of a downwardly tapering regular polygonal pyramid, or a shape of an upwardly tapering regular polygonal pyramid;
the top is one of a planar end cap, an inner cavity of the top is a part of a spherical surface, or an inner cavity of the top is a part of an ellipsoidal surface with a: b: c at any ratio;
a largest continuous gap formed between the top and the body is less than ½-⅓ of the area of the smallest one of the PET detection crystals;
a coincidence circuit is connected between every two PET detection modules;
each of the PET detection modules comprises:
a detector housing,
a photoelectric sensor array,
a light guide, and
wherein the PET detection crystals are sequentially arranged from outside to inside, and the light guide is tightly coupled with both the photoelectric sensor array and the PET detection crystals;
the material of the PET detection crystals is a scintillation crystal comprising one or more crystal blocks;
the regular polygonal prism is a regular hexagonal prism or a regular octagonal prism, and the regular polygonal pyramid is a regular quadrangular pyramid or a regular hexagonal pyramid; and
a circular ring-shaped shielding plate is attached closely against a lower edge of the body, the material of the shielding plate is stainless steel or boron-containing plastic or lead-containing plastic, and the shielding plate is formed by splicing two to five sub-plates having exactly the same shape.

2. The overall full-angle coincidence brain PET detector according to claim 1, wherein:
the detection cavity formed by the top and the body is one of a sphere shape or an ellipsoid shape;
the sphere shape having axes of all the PET detection modules pass through a center of the sphere, and distances from centers of inner surfaces of all the PET detection modules to the center of the sphere are equal or have an error within 8 mm; and
the ellipsoid shape having an ellipsoid shape with c>a=b is formed in the inner cavity of the detection cavity.

3. An overall full-angle coincidence brain PET detector: comprising:
a plurality of PET detection modules, each of which comprising:
PET detection crystals,
a photoelectric sensor array, and
a light guide,
wherein the PET detection crystals being each arranged in a direction toward an interior of a detection cavity;
wherein the plurality of PET detection modules are adjacent to each other to form the detection cavity with an opening, a length, width and height of an inner cavity of the detection cavity are no larger than 35-50 cm each, the opening of the detection cavity is located below the detection cavity, and the cross-sectional area at the opening is larger than a maximum cross-sectional area of human head in a horizontal direction;
wherein except for the opening, all the plurality of PET detection modules are non-detachably connected together; and a cross-sectional area of each of gaps between the plurality of PET detection modules is less than ½-⅓ of an area of a smallest one of the PET detection crystals;
a detection coverage of the detection cavity for true coincidence events reaches such a degree that at least 75%-80% of the true coincidence events occurring from a center of the detection cavity are detected by the plurality of PET detection modules;
the detection cavity is formed by splicing a top and a body with different geometric shapes;
the body has one of a shape of a middle part of a sphere, a shape of an ellipsoid with c>a=b and a part of the top and a part of the bottom removed respectively, a shape of a regular polygonal prism, a shape of a cylinder, a shape of a downwardly tapering truncated cone, a shape of an upwardly tapering truncated cone, a shape of a downwardly tapering regular polygonal pyramid, or a shape of an upwardly tapering regular polygonal pyramid;
the top is one of a planar end cap, an inner cavity of the top is a part of a spherical surface, or an inner cavity of the top is a part of an ellipsoidal surface with a: b: c at any ratio;

a largest continuous gap formed between the top and the body is less than ½-⅓ of the area of the smallest one of the PET detection crystals; and several PET detection modules that are slightly higher on the front portion of the detection cavity are removed to form an opening suitable for both eyes to observe outward.

4. The overall full-angle coincidence brain PET detector according to claim 3, wherein:

inward faces of the PET detection crystals are planar or nearly planar, and the shapes are square or rectangle;

the crystal block is specifically a crystal strip array comprising one of a plurality of crystal strips, or one or more integrally cut crystals;

a material of the scintillation crystal is selected from one or more of bismuth germanate (BGO) crystals, sodium iodide (NaI) crystals, NaI(Tl) single crystals, lutetium silicate (LSO) crystals, gadolinium silicate (GSO) crystals and yttrium lutetium silicate (LYSO);

spacers made of high atomic number substance are installed between all the detection module rings, or spacers made of high atomic number substance are installed between some of the detection module rings, or no spacers are installed between all the detection module rings;

the high atomic number substance is lead or tungsten, the regular polygonal prism is a regular hexagonal prism or a regular octagonal prism, and the regular polygon is a regular hexagon or a regular octagon.

5. The overall full-angle coincidence brain PET detector according to claim 4, wherein the crystal strip array comprises a plurality of crystal strips; and each of the one or more crystal blocks comprises one or more integrally cut crystals.

6. An overall full-angle coincidence PET detection apparatus, comprising:

a full-angle coincidence PET detector comprising:

a plurality of PET detection modules, each of which comprising:

PET detection crystals, a photoelectric sensor array, and a light guide, wherein the PET detection crystals being each arranged in a direction toward an interior of a detection cavity;

wherein the plurality of PET detection modules are adjacent to each other to form the detection cavity with an opening, a length, width and height of an inner cavity of the detection cavity are no larger than 35-50 cm each, the opening of the detection cavity is located below the detection cavity, and the cross-sectional area at the opening is larger than a maximum cross-sectional area of human head in a horizontal direction;

wherein except for the opening, all the plurality of PET detection modules are non-detachably connected together; and a cross-sectional area of each of gaps between the plurality of PET detection modules is less than ½-⅓ of an area of a smallest one of the PET detection crystals; and a support member, a power supply circuit, a communication line, and a PC terminal;

wherein the support member fixes and supports all the plurality of PET detection modules on the aforementioned detection cavity, and the support member can drive the detection cavity to rotate at any angle, or drive the detection cavity to translate toward any direction;

the PC terminal is equipped with a PET signal acquisition and operation analysis system;

the power supply circuit provides an electrical energy under a rated voltage to the support member and all the PET detection modules; and the communication line transmits signals detected by all the PET detection modules to the PET signal acquisition and operation analysis system.

* * * * *